(12) United States Patent
Queen

(10) Patent No.: US 7,926,322 B1
(45) Date of Patent: Apr. 19, 2011

(54) OXYGEN SENSING SYSTEM

(75) Inventor: James C. Queen, Arden, NC (US)

(73) Assignee: EII, LLC, Bryson City, NC (US)

( * ) Notice: Subject to any disclaimer, the term of this patent is extended or adjusted under 35 U.S.C. 154(b) by 381 days.

(21) Appl. No.: 11/983,598

(22) Filed: Nov. 9, 2007

Related U.S. Application Data

(60) Provisional application No. 60/858,040, filed on Nov. 9, 2006.

(51) Int. Cl.
*G01N 21/00* (2006.01)

(52) U.S. Cl. ........................................ 73/1.02

(58) Field of Classification Search .................. 73/1.02; 359/838; 378/84; 356/70
See application file for complete search history.

(56) References Cited

U.S. PATENT DOCUMENTS

| | | | | |
|---|---|---|---|---|
| 5,060,505 A | * | 10/1991 | Tury et al. | 250/343 |
| 5,887,048 A | * | 3/1999 | Sata et al. | 378/84 |
| 6,205,272 B1 | * | 3/2001 | O'Rourke et al. | 385/33 |
| 2006/0018045 A1 | * | 1/2006 | Moeller et al. | 359/838 |

* cited by examiner

*Primary Examiner* — Hezron Williams
*Assistant Examiner* — Tamiko D Bellamy
(74) *Attorney, Agent, or Firm* — Smith Moore Leatherwood LLP; Thomas W. Epting

(57) ABSTRACT

A system of measuring oxygen levels based on the intensity of a sensor material. Through use of intensity-based measurement techniques and improved light rejection, less excitation light and system gain are required as compared to certain conventional lifetime/phase shift techniques. One embodiment applies an intensity-based measuring system for taking measurements, and on an intermittent basis, using a lifetime/phase shift-type sensor in order to automatically calibrate the intensity-based measuring system in situ. A single sensing membrane may be provided while still allowing the system to be used in both the lifetime/phase-shift mode and the intensity mode. The system of the present invention may also include use of a variable thickness sensor for an oxygen sensing system, such as a portable handheld sensor and/or a sensor or controller at a fixed location.

5 Claims, 14 Drawing Sheets

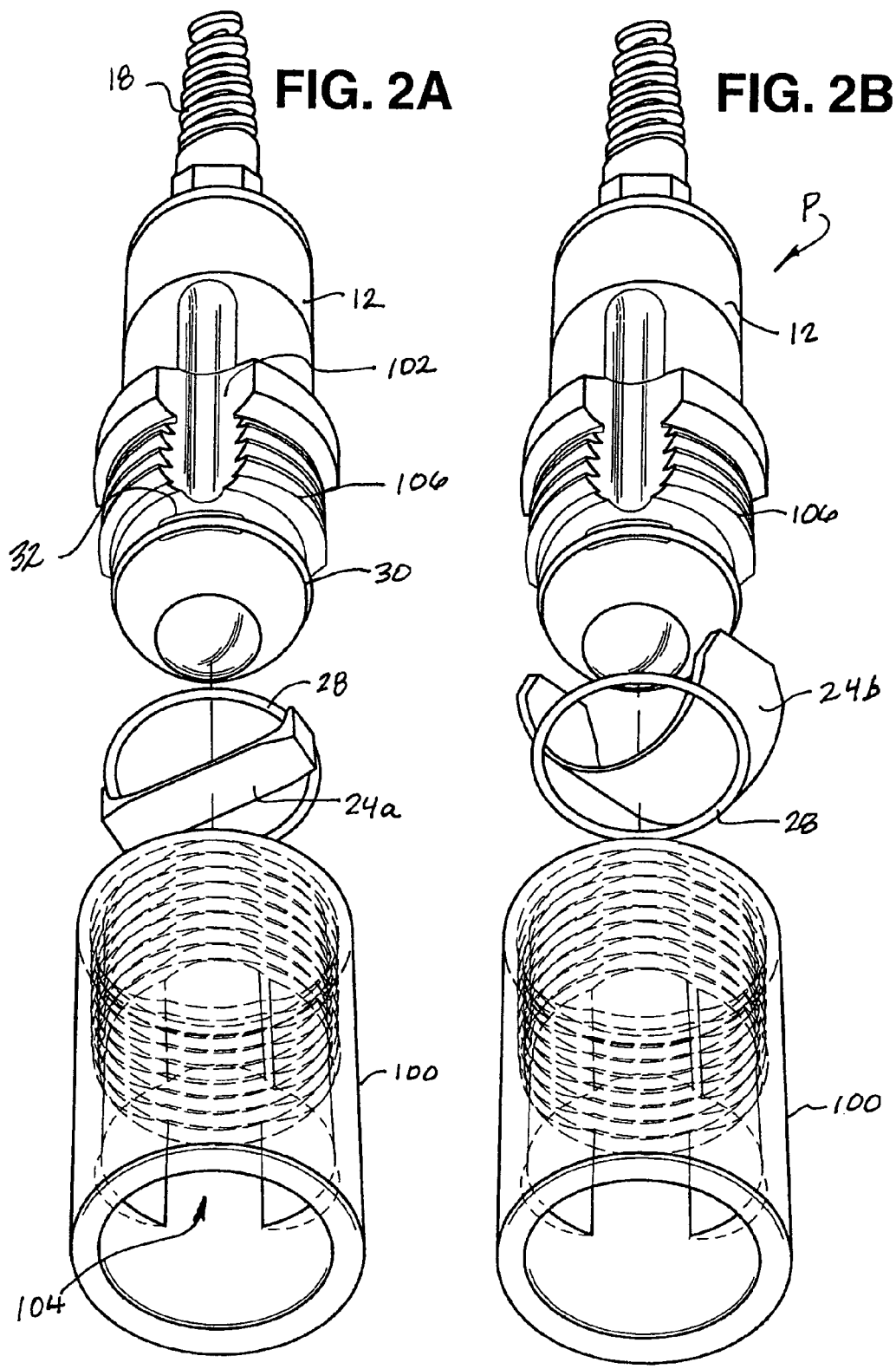

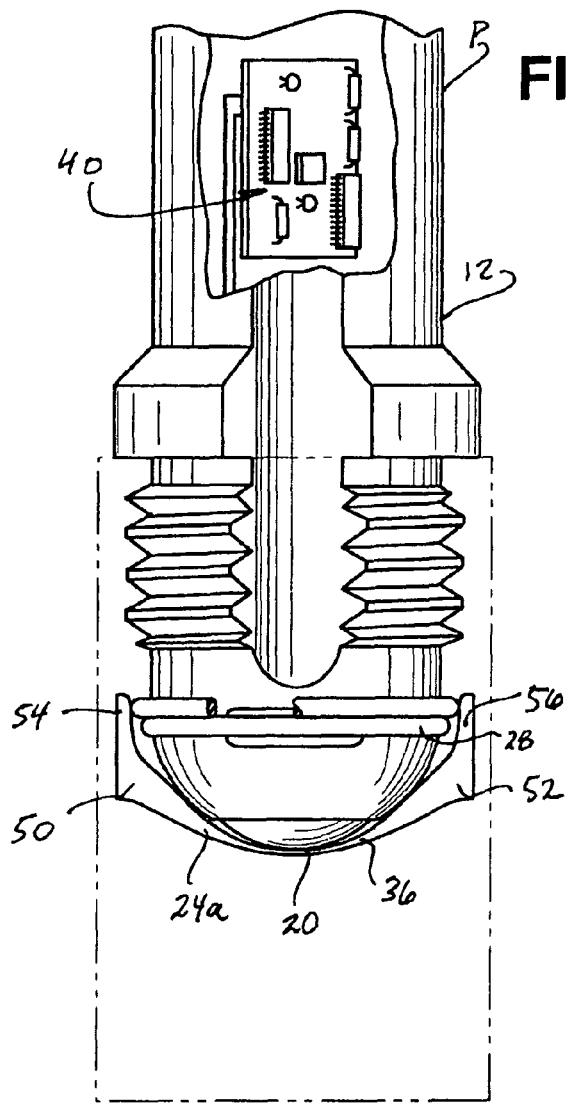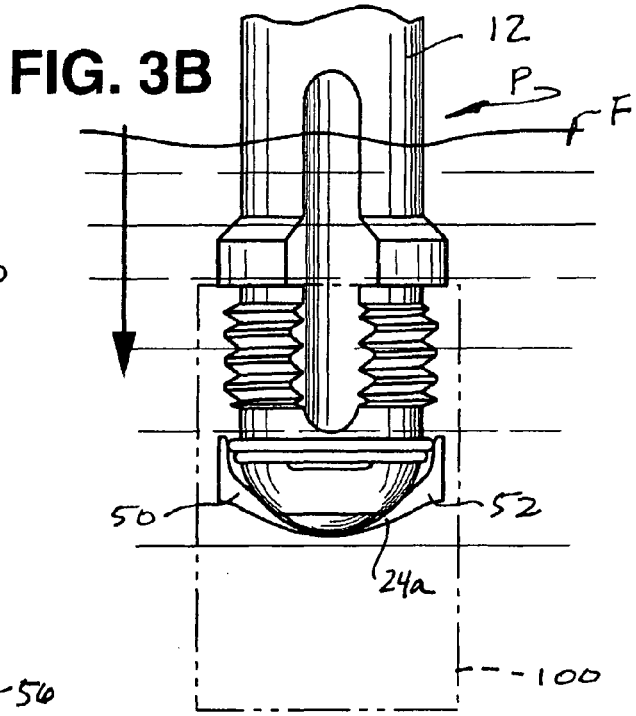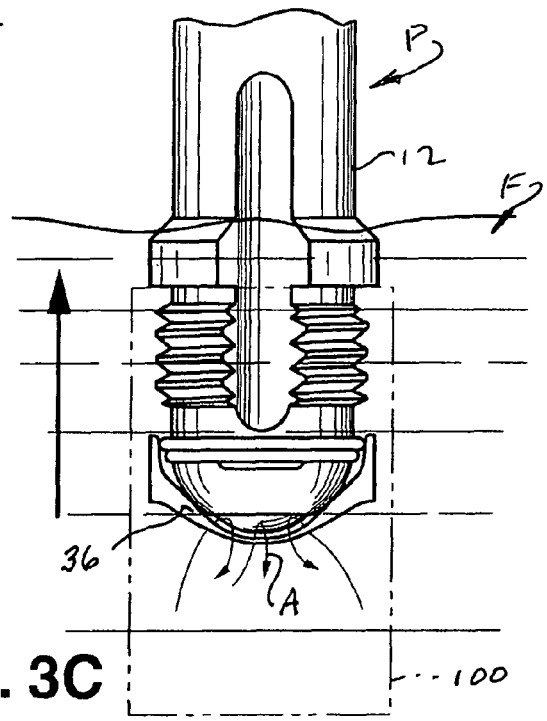
FIG. 3A
FIG. 3B
FIG. 3C

OXYGEN SENSING SYSTEM

This application claims benefit of U.S. Provisional application Ser. No. 60/858,040, filed Nov. 9, 2006, and the entirety of the foregoing application is incorporated herein by reference thereto.

BACKGROUND OF THE INVENTION

This invention relates generally to a sensing system for detecting and measuring a constituent, such as oxygen, within a fluid, and more particularly, for detecting oxygen concentration levels in aqueous samples, gaseous samples, and biological samples.

A know method of measuring oxygen involves use of sensors applying lifetime/phase shift measurement techniques. Lifetime/phase shift measurement techniques generally provide, after proper calibration and provided there is a threshold level of light intensity being supplied to a sensor, a relatively absolute output correlating to concentration of oxygen. Variations in intensity above that threshold level ordinarily have little or no effect on the output of such lifetime/phase shift sensor.

However, disadvantages of lifetime/phase shift sensors ordinarily include a potential for degradation of the sensor over time, due to photo-bleaching of the sensor material. Accordingly, accommodations must be made for rejecting unwarranted ambient light from the sensor. Another potential disadvantage of the lifetime/phase shift-type sensor is that due to the typical inherent high-frequency operation of the probe, the sensor is of a certain sophistication, which may increase costs and manufacturing complexities. Also, high frequency operation of the probe typically requires accommodation for noise isolation, dielectric problems, interference, etc.

Also, with such lifetime/phase shift-type sensors, as oxygen increases, the signal-to-noise ratio may increase to the point where the signal is no longer obtainable, since the intensity threshold is below that which will give a meaningful lifetime/phase shift measurement.

SUMMARY OF THE INVENTION

Generally, the present invention includes a system of measuring oxygen levels based on the intensity of the sensor material. Well-developed, off-the-shelf, and generally less expensive, detectors can be used as components of the system, as well as less sophisticated electronics, as compared to existing sensors. A processor and associated software is provided in one preferred embodiment of the present invention, although such processor and software are not necessarily required. At a basic level, the human eye could be used as a suitable detector of the sensor's status.

The system of the present invention, through use intensity-based measurement techniques, also allows for improved light rejection, since less system gain is required as compared to lifetime/phase shift techniques, and, further, less excitation light is required. The intensity-based system of the present invention requires, as compared to the lifetime/phase shift system, relatively little light exposure on the sensor in order to obtain a reading. In other words, less excitation of the sensor is necessary for a usable output, thus leading to less photo-bleaching and to longer sensor life. In the case of a handheld instrument constructed in accordance with the present invention, battery life may also be improved.

Additionally, an intensity-based system constructed in accordance with the present invention allows for an expanded range of measurement of oxygen, as compared to lifetime/phase shift-type sensors.

One preferred embodiment of the present invention applies an intensity-based measuring system as its prime measurement means, but also uses on an intermittent basis a lifetime/phase shift-type sensor in order to automatically calibrate the intensity based system in situ. In another preferred embodiment, only one membrane need be provided, and a combination of hardware and software allow the sensing system of the present invention to be used in both modes, both the lifetime/phase-shift mode and the intensity mode.

The present invention also includes a method for in situ self calibration using phase shift and intensity-based measurements in relation to indicator compounds, such as oxygen, utilizing quenching relative to fluorescence for quantification.

The present invention could potentially find use in the detection and measurement of pH, carbon monoxide, and various gases, aqueous components, elemental components, and macromolecular components, including, but not limited to, in the genetics and the biotech industries.

The system of the present invention also includes use of a variable thickness sensor portion for an oxygen sensing system, such as a handheld sensor and/or a permanent, in-place type of sensor or controller. In one preferred embodiment, the variable thickness sensor of the present invention is affixed to an O-ring using silicone adhesive. The membrane is thickest about the margins, or perimeter portions, and thinnest at a central portion, perhaps on the order of 0.003 inches. The thinnest portion of the membrane is configured for being adjacent a lens of the probe, which is used to focus blue light emitting diode (LED) excitation light onto the membrane. The reflection of such light off of the membrane is measured, and the measurement corresponds to the oxygen concentration in the fluid.

The thicker portions of the membrane provide, in effect, a store, or "reservoir" of material from which to draw additional membrane material as the adjacent thinner portions of the membrane are stretched upon application to the sensor, and thus the thicker portions provide a means for relieving the stresses experienced by the thinner portions.

Preferably, the thicker portions of the membrane are resilient in nature and act to absorb, or take up, thermal growth in the thinner portions of the membrane, such that the thinner portions of the membrane maintain proper positioning with respect to the sensor upon changes in temperature. Preferably, in certain embodiments, the membrane is configured to permit water or other fluid being measured is permitted to pass between the membrane and the end of the probe.

In one preferred embodiment, the sensor membrane is stretched over a convex lens used to focus the LED light on the sensor, and allows for the advantage of having flow both beneath and above the sensing membrane. Another aspect is that as the sensor is moved up and down during the taking of a measurement using one measurement technique, the sensor tends to separate from the lens and substantially "balloon" outwardly away from the lens, and this allows for water or other material to effectively be pumped through the interface between the bottom surface of the sensor and the lens.

It is to be understood that instead of a convex lens, some arcuate, curved, other smooth transitioned surface could be used, the goal being to focus the light emitted from the LED onto a concentrated point on the sensor membrane. This also allows the light to be focused at the point of maximum exposure of the lens, i.e., where the lens sees the maximum amount of movement of fluid as the probe is oscillated upwardly and downwardly.

As noted above, the membrane is preferably stretched over the lens during installation. However, the membrane is allowed to balloon, or "parachute" away from the lens as the probe is moved, while rebounding or returning to the original position contacting the convex lens or curved surface to allow measurements to be taken.

The system of the present invention further includes a handheld oxygen sensing probe able to be read while being oscillated within the fluid source, or while being maintained stationary in such fluid source. A collar is provided for reducing ambient light exposure onto a sensor carried by the handheld probe, while still allowing adequate flow of fluid around the end of the probe for taking accurate readings.

In one preferred embodiment, the hand-held probe of the present invention includes elongated channels extending longitudinally about the circumference of the probe and in the interior of the collar. These channels are adjacent threaded lands, and a collar is threadingly engaged with the threaded lands of the probe. The channels allow water to flow to and fro therein as the probe is oscillated in a fluid source while taking a measurement. Alternately, as noted above, if the probe is static while taking measurements, the fluid can come into contact with the sensor. In one preferred embodiment, the collar extends outwardly beyond the extreme end of the sensor.

The collar allows fluid flow to be improved around the sensor, i.e., on both sides of the sensing membrane, thereby improving the measurement technique, and also simultaneously diminishes undesirable ambient light exposure to the sensor.

In an alternate embodiment, the collar could be provided, if desired, with a flexible membrane or adjustable aperture at the open end of the collar in order to further reduce ambient light exposure to the sensor.

BRIEF DESCRIPTION OF THE DRAWINGS

The foregoing, as well as other objects of the present invention, will be further apparent from the following detailed description of the preferred embodiment of the invention, when taken together with the accompanying specification and the drawings, in which:

FIG. 2A is an exploded view of a probe embodying an oxygen sensing system constructed in accordance with the present invention having a collar and a membrane member;

FIG. 2B is a perspective view of a probe such as illustrated in FIG. 2A having a first alternate embodiment membrane member;

FIG. 3A is a side elevational view, with parts cut away, of the probe illustrated in FIG. 2A;

FIG. 3B is a side elevational view of the probe illustrated in FIG. 3A illustrating the probe being moved downwardly within fluid, and wherein a membrane member is generally contacting a lens of the probe;

FIG. 3C is a side elevational view of the probe illustrated in FIG. 3B being moved upwardly within the body of fluid, wherein there is a gap between the membrane and the lens such that fluid may flow therebetween;

DESCRIPTION OF THE PREFERRED EMBODIMENT

Figure 1:
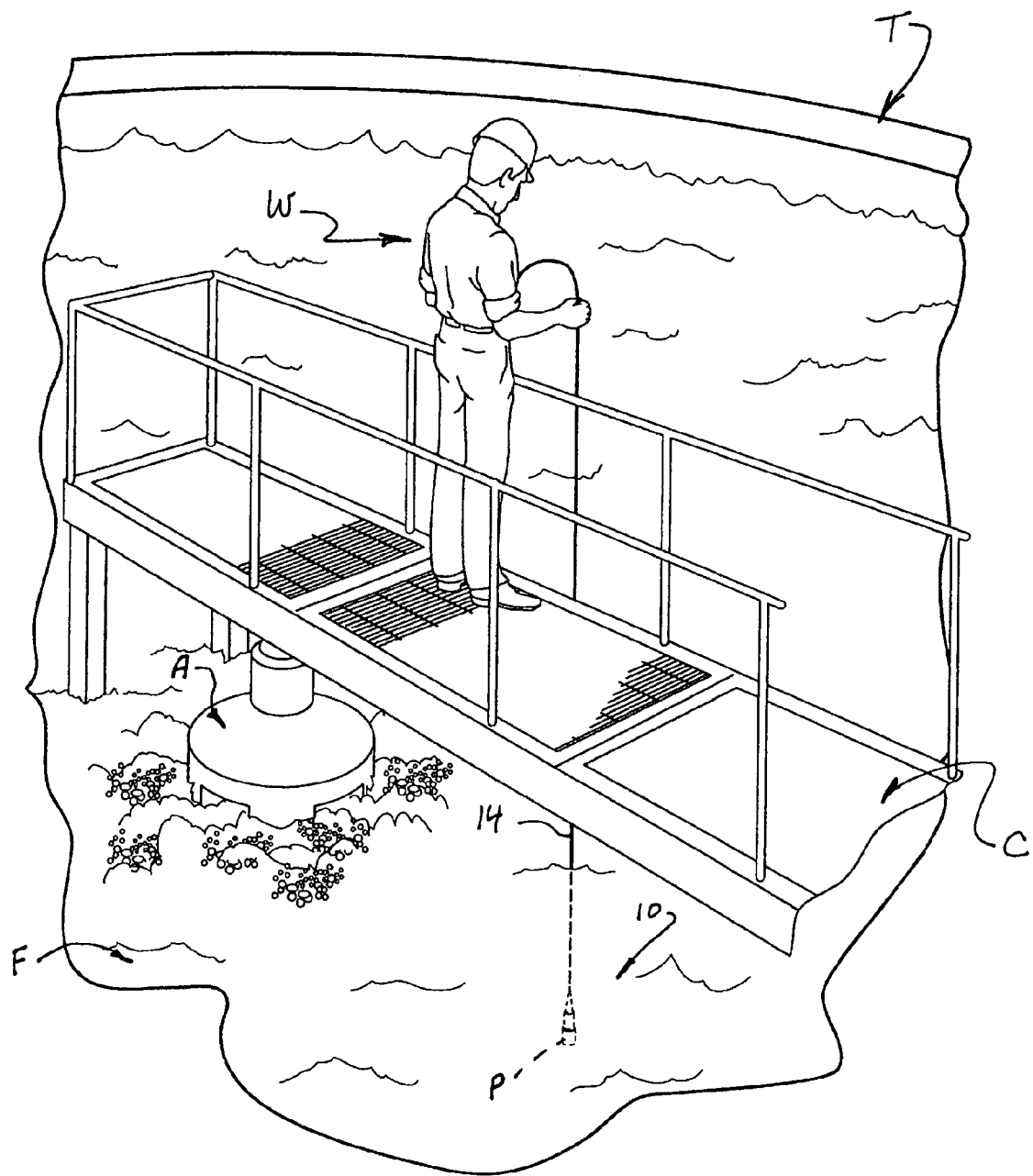
FIG. 1 is an exploded view of a probe embodying an oxygen sensing system constructed in accordance with the present invention.

The accompanying drawings and the description which follows set forth this invention in its preferred embodiment.

However, it is contemplated that persons generally familiar with oxygen and other constituent detection and measurement devices will be able to apply the novel characteristics of the structures illustrated and described herein in other contexts by modification of certain details. Accordingly, the drawings and description are not to be taken as restrictive on the scope of this invention, but are to be understood as broad and general teachings.

Referring now to the drawings in detail, wherein like reference characters represent like elements or features throughout the various views, the sensing system of the present invention is indicated generally in the figures by reference character 10.

Turning to FIG. 1 of the drawings, sensing system 10 is illustrated in use with a fluid tank, such as a sewage treatment tank, generally T. It is to be understood, however, that sensing system 10 can be used in variety of other applications where oxygen, or other constituent, levels are to be sensed within a fluid, including, but not limited to, industrial processes, medical applications, and/or environmental monitoring applications of streams, rivers, lakes, etc.

A worker, generally W, is shown on a catwalk, generally C, above tank T. A probe, generally P, is shown immersed into the fluid, generally F, probe P being suspended by an electrical/communication cable providing the output from probe P.

In the application shown in FIG. 1, probe P may be used for detecting oxygen levels within treated sewage being aerated by an aerator, generally A. As noted above, the present invention 10 is not limited, however, to use in connection with sensing of oxygen alone or to sewage treatment applications.

Figure 4A:
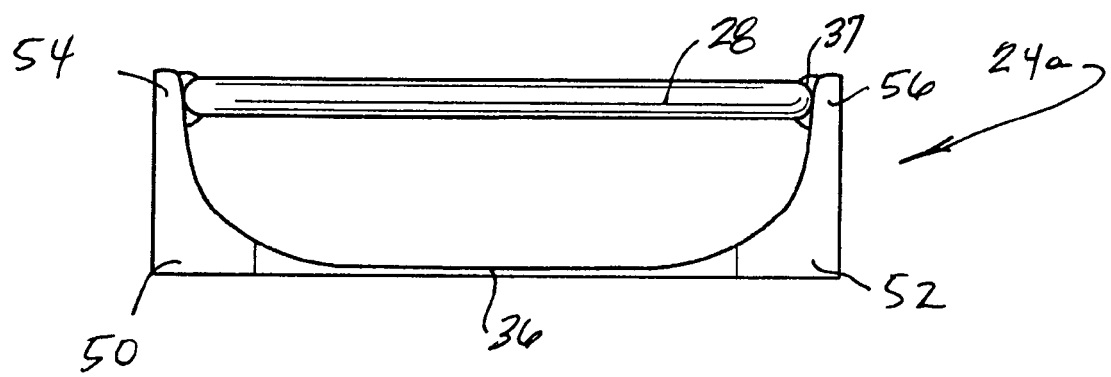
FIG. 4A is a side elevational view of the membrane member illustrated in FIG. 2A.
Figure 4B:
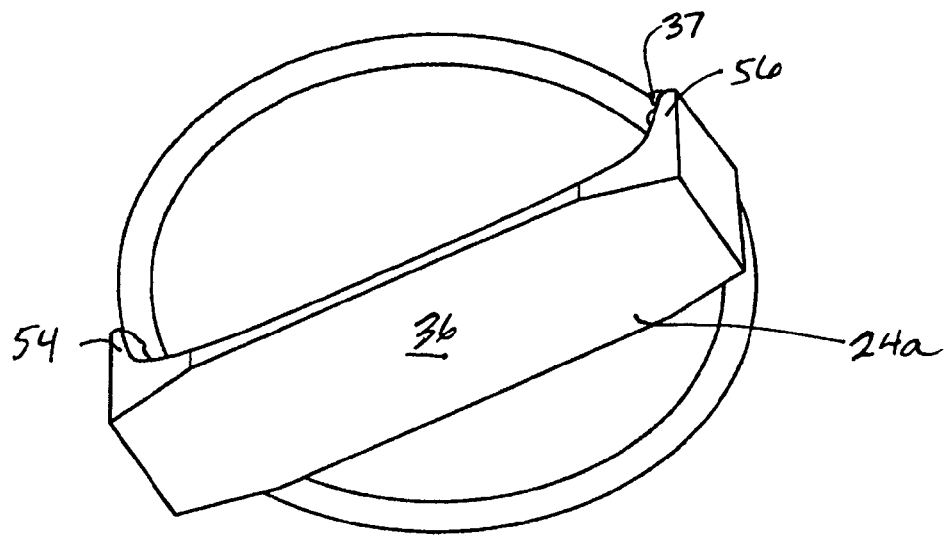
FIG. 4B is a perspective view of the membrane member illustrated in FIG. 4A.

FIG. 2A illustrates probe P in more detail. Probe P includes a body portion, generally 12, which is of a generally cylindrical shape having at one end thereof a connection with cable 14 (FIG. 1). Cable 14 is received in a cable strain relief device 18, and at the other end thereof, a lens, generally 20, for focusing an excitation light from a light source, generally 22 (FIG. 12), onto a membrane, or membrane member, generally 24a. Membrane 24a is also shown in FIGS. 4A and 4B and is preferably constructed of a silicone-based material such as disclosed in U.S. Pat. No. 5,030,420, the entirety of such patent being incorporated herein by reference.

One such suitable silicone-based material is a silicone/ruthenium material which, while having a certain amount of elasticity, can be delicate and easily torn. Membrane member 24a is attached to an elastomeric O-ring, generally 28, which is received within a groove 30 of the forward end of probe P. Groove 30 extends circumferentially about this end of probe P, and includes a recess, generally 32, for allowing a tool, the user's fingernail, etc., access to O-ring 28 in order for installing and/or removing O-ring 28 from groove 30, when desired. Membrane member 24a is attached to O-ring 28 through use of a suitable silicone-based adhesive.

FIG. 2B shows a first alternate embodiment membrane member 24b, which has a generally uniform cross-section along its length. Membrane member 24b is held in place on the end of probe P by O-ring 28 being placed on top of member 24b and both member 24b and O-ring 28 being received in groove 30 of probe P.

Figure 2C:
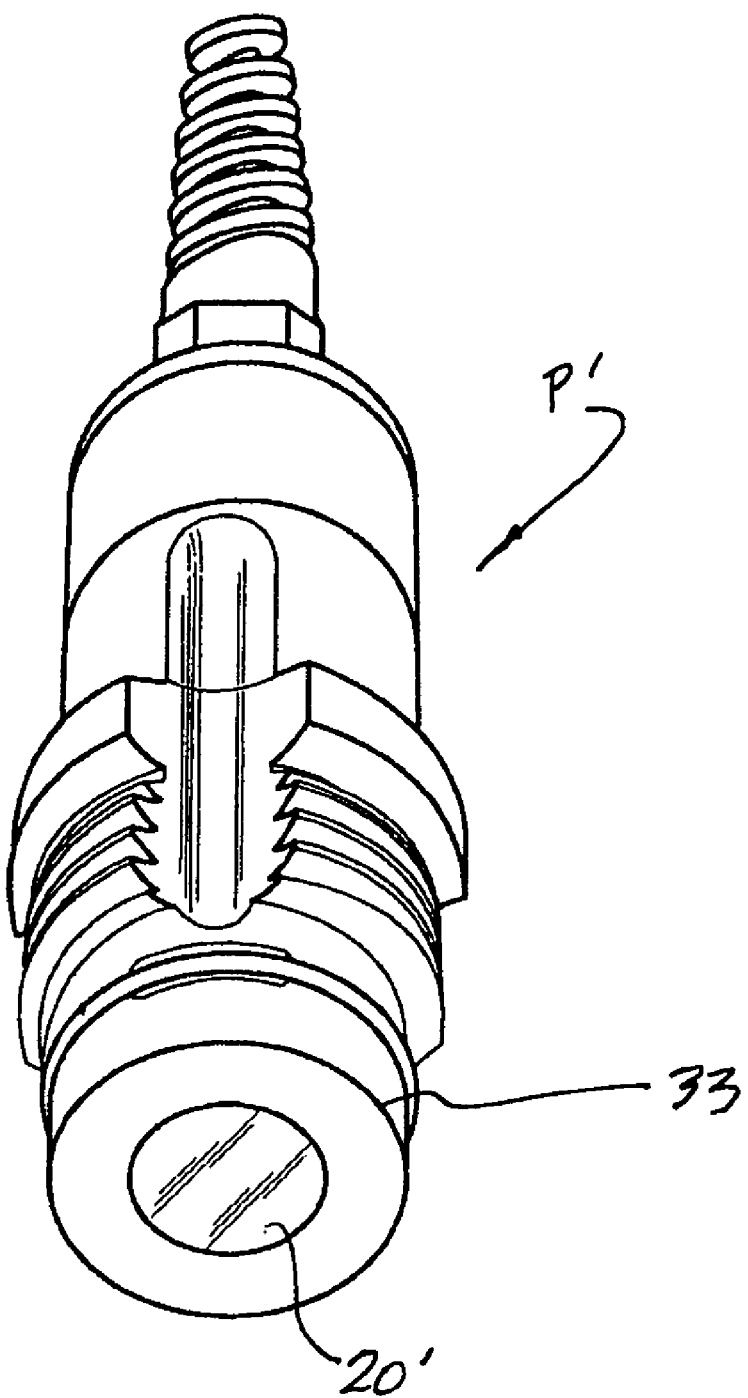
FIG. 2C is a perspective view of a alternate embodiment probe embodying the oxygen sensing system of the present invention.

FIG. 2C shows probe P', an alternate embodiment, wherein lens 20' is flat as is also the end 33 of probe P'. In this embodiment, a membrane constructed in accordance with the present invention can be provided in a cap (not shown) which is snapped into place on end 33, the cap engaging groove 30 for releasably maintaining the membrane in place over lens 20'.

FIG. 3A illustrates membrane 24a and O-ring 28 seated on the forward end of probe P, with a central portion 36 being stretched over, and in contact with, lens 20. FIG. 3A also illustrates membrane member 24a when viewed from the side and shows how the thickness of membrane 24a varies across its length. The thinnest portion of membrane 24a is that portion which is the central portion 36, adjacent lens 20. The thinner the membrane 24a, and in particular, central portion 36 thereof, generally the faster the response time of probe P, through use of the electronic circuitry, or, "electronics," generally 40, of probe P.

Because of the nature of membrane 24a, and because it is desirable to make the membrane portion 36 as thin as practicable in order to lessen the response time of probe P, a problem may arise in the handling of membrane 24a in a manner which prevents it from being torn or damaged during installation on and/or removal from the end of probe P. While the end of probe P is, in one preferred embodiment, generally hemispherical in shape, such that it does not present sharp edges to membrane 24a, the silicone/ruthenium construction of one preferred embodiment of membrane 24a nevertheless may be relatively delicate and prone to tearing.

As noted above, the desired smooth transition of the end of the probe eliminates a pinch-point, or sharp corner, which could be more apt to cut or tear the membrane, and serves to reduce the risk of the membrane tearing upon installation. Since the membrane generally is stretched over the end of the probe during installation of the membrane, having the extra material in the thicker marginal portions 50, 52, discussed below, facilitates proper installation of the membrane while reducing the risk of the membrane breaking during installation.

Figure 15:
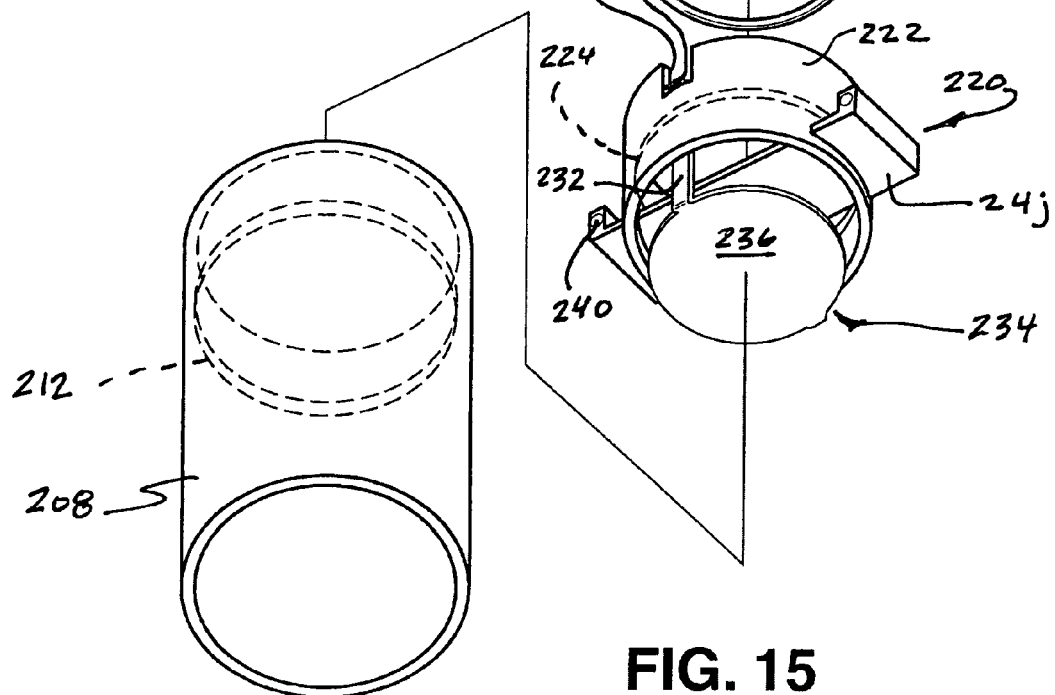
FIG. 15 is exploded view of a fifth alternate embodiment probe embodying the oxygen sensing system of the present invention, including a combination guard member and ring member for attachment to the probe.

Alternately, instead of having the smooth transaction of the end of the probe, the end of the probe could be configured with oblique radial ridges 41 as shown in FIG. 15 and/or in a number of other different ways, and could include other attachment configurations, such as shown in FIGS. 10A, 10B, and 13A-13D, or otherwise. It is to be understood that the present invention is not to be limited to the membrane profiles and configurations specifically disclosed herein, and that the membrane and its attachment to the probe could take on a variety of configurations or arrangements.

In order to reduce the chance of such tearing, and in addition to providing a smooth transition at the end of probe P by virtue of the hemispherical shape, and eliminating pinch points, sharp edges, etc., membrane 24a also includes extra material in margin portions, generally 50, 52, outboard of central portion 36 which, when membrane 24a is stretched over the end of probe P during installation, reduces the likelihood of membrane 24a breaking. The extra material embodied in thicker portions 50, 52 also provides a resilient effect in maintaining membrane 24a generally against lens 20 through temperature variations within which probe P may operate. Portions 50, 52 of membrane 24a provide, in effect, a store or reservoir of material from which to draw as the central portion 36 and portions adjacent thereto are stretched upon application to the end of probe P. Portions 50, 52, accordingly, provide a means for relieving the stresses experienced by such thinner portions and reduce the chance of breakage of membrane 24a.

Also, portions 50, 52, being resilient in nature, act to absorb and take up thermal growth in the thinner portions of membrane 24a, such that such thinner portions maintain proper positioning with respect to lens 20, and accordingly, excitation light source 22, during use. Extending downwardly from portions 50, 52 are flanges 54, 56, respectively, which are attached to O-ring 28, in one preferred embodiment, with adhesive 37 (FIGS. 4A and 4B).

As shown in FIGS. 3B and 3C, probe P may be used in certain applications in a manner wherein it is oscillated upwardly and downwardly in order to take oxygen readings from a fluid. FIG. 3B illustrates probe P on a downward stroke, with central portion 36 of membrane 24a against lens 20. FIG. 3C illustrates probe P on an upward stroke, wherein central portion 36 of membrane 24a has pulled away, or "ballooned" slightly away from the surface of lens 20a, allowing fluid to flow therebetween in a manner as shown by arrows A. By allowing fluid to flow through the interface between the surface of lens 20 and central portion 36, additional fluid sampling is in effect achieved, to enhance the accuracy of oxygen readings provided by probe P.

As shown in FIGS. 2A, 3A, 3A-3C, 4A, 5A, 6A, and 6B, portions 50, 52 of membrane 24a are attached to O-ring 28 by being molded integrally therewith (FIG. 5A), or, by attachment thereto using an adhesive (FIGS. 2A, 3A-3C, 4A, 4B, 6A, and 6B), such as a silicone adhesive. Portion 36 of membrane 24a is, as noted above, as thin as practical from a manufacturing and handling standpoint, and is preferably on the order of between 0.001 and 0.005 inches thick. When membrane portion 36 is adjacent the convex profile of lens 20 and receives blue LED excitation light from excitation light source 22, focused on portion 36, the reflection of such light off portion 26 is detected and measured, using electronics 40 (FIG. 3A), and such measurement corresponds to the oxygen (or other constituent) concentration of the fluid (gas and/or liquid) to which probe P is exposed. The technique by which the reflection of the blue light off of membrane portion 36 is used to measure oxygen levels is discussed in detail in U.S. Pat. No. 5,030,420, issued to Bacon, et al. (the "Bacon et al. patent"), and the entirety of such patent is incorporated herein by reference. AS referenced above, the membrane material is preferably a silicone-based material, such as disclosed in the Bacon et al. patent. Note with respect to the Bacon et al. patent, "quenching" is a term that refers to the lowered output of a lifetime/phase-shift sensor as higher oxygen concentrations are sensed.

It is also to be understood that instead of a convex profile, lens 20 could have other profiles, such as a flat profile, as shown by lens 20A in FIG. 2C, or could have a convex, or other (not shown).

Figure 5A:
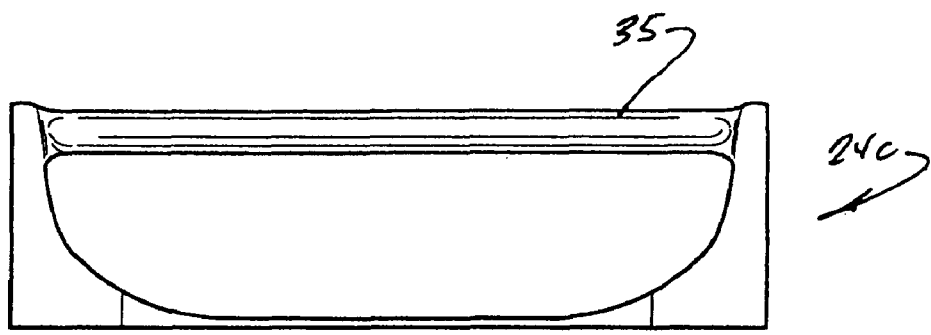
FIG. 5A is a side elevational view of a second alternate embodiment membrane constructed in accordance with the present invention.

FIG. 5A illustrates another alternate embodiment of a membrane member constructed in accordance with the present invention. Membrane member 24c includes an O-ring type portion 35 integrally molded to member 24c. Portion 35 can be received in groove 30 of probe P to properly position portion 36c over lens 20 of probe P.

Figure 5B:
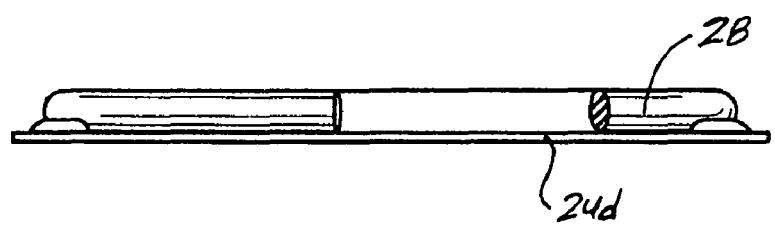
FIG. 5B is a side elevational view, with parts cut away, of a third alternate embodiment membrane constructed in accordance with the present invention.
Figure 5C:
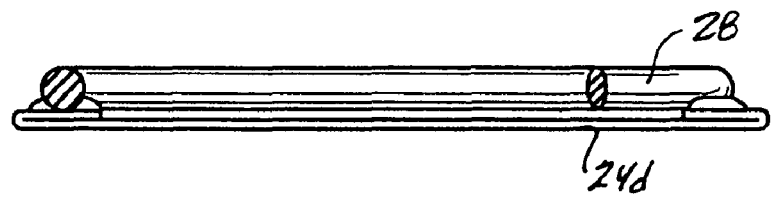
FIG. 5C is a side elevational view, with parts cut away, of a fourth alternate embodiment membrane constructed in accordance with the present invention.

FIG. 5B illustrates another alternate embodiment of a membrane member constructed in accordance with the present invention. Membrane member 24d is of generally uniform cross-section and is attached to O-ring 28 via adhesive 37.

FIG. 5B illustrates another alternate embodiment of a membrane member 24d attached to O-ring 28 by adhesive 37 and is of generally uniform cross-section like membrane member 24c discussed above. However, membrane 24d has ends 60, 62 which are folded over onto themselves, and these folded-over ends attached to O-ring 28. The folded-over ends 60, 62 act as reservoirs of extra membrane material and in similar manner as do portions 50, 52 discussed above with respect to membrane member 24a.

Figure 6A:
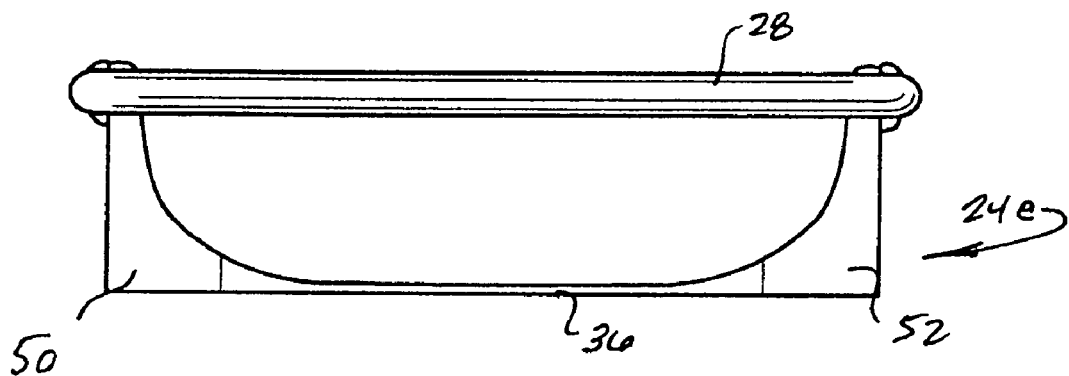
FIG. 6A is a side elevational view of a fifth alternate embodiment membrane constructed in accordance with the present invention.
Figure 6B:
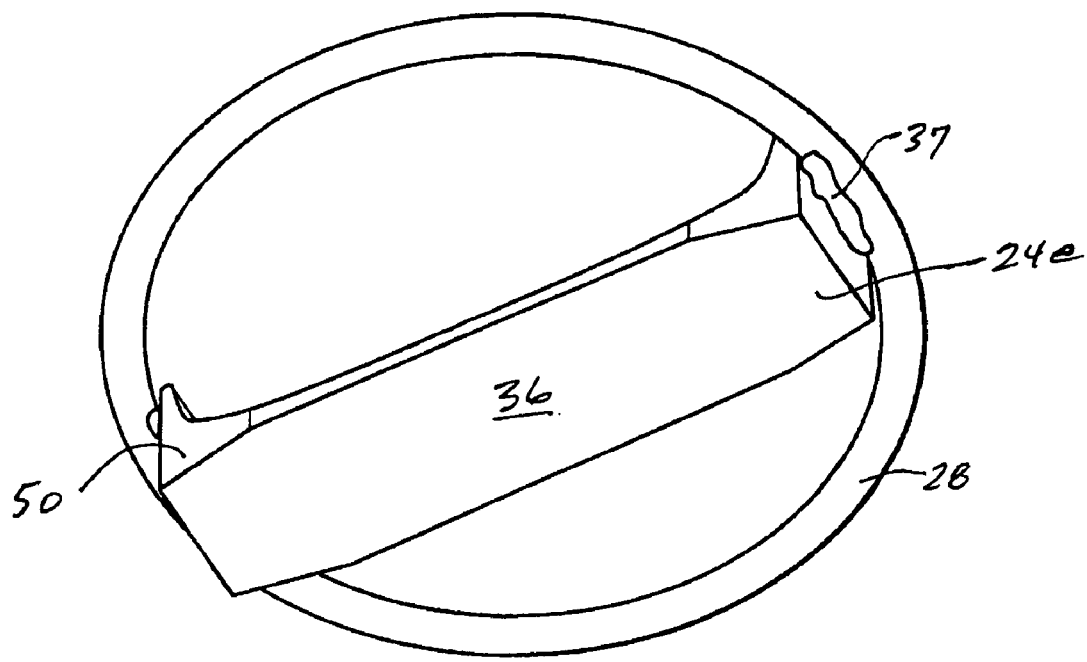
FIG. 6B is a perspective view of the fifth alternate embodiment membrane illustrated in FIG. 6A.

FIGS. 6A and 6B illustrate another alternate embodiment membrane, namely, membrane member 24e. Membrane 24e attached to O-ring 28 with adhesive 37. As compared to membrane 24a, the ends of membrane 24d are positioned within O-ring 28, instead of outside of O-ring 28, as is the case with membrane 24a (FIGS. 2A, 3A-3C, 4A, and 4B).

Figure 7:
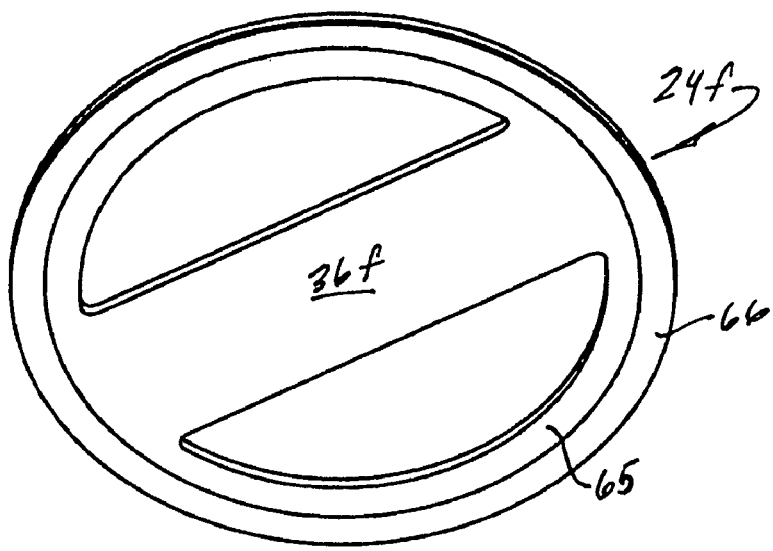
FIG. 7 is a perspective view of a sixth alternate embodiment membrane constructed in accordance with the present invention.

FIG. 7 shows a further alternate embodiment membrane, membrane 24f, having a central portion 36f integral with a circumferential portion, 65, to which a resilient ring portion, generally, 66, is connected. Resilient ring portion 65 is received, in use, in groove 30 of probe P.

Figure 8:
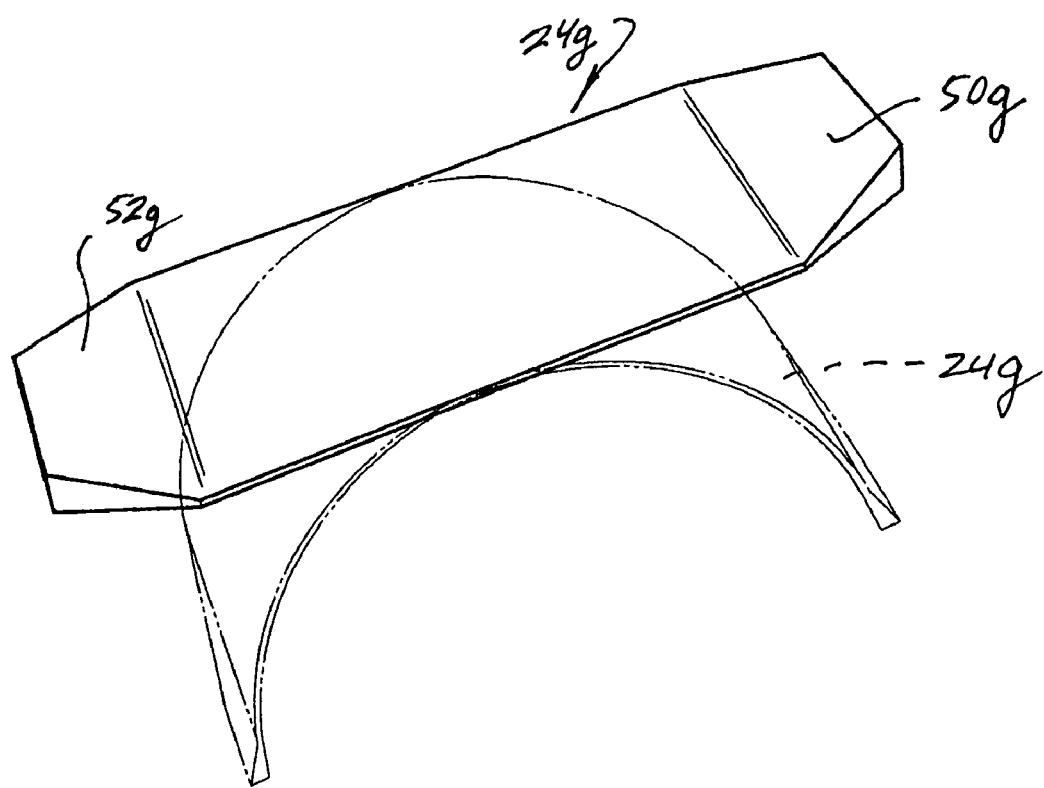
FIG. 8 is a perspective view of the first alternate embodiment membrane illustrated in FIG. 2B.
Figure 9A:
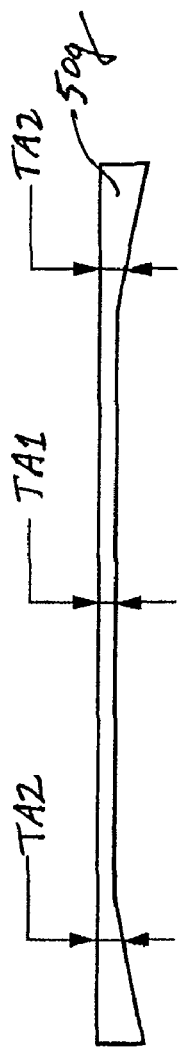
FIG. 9A is a sectional view of a membrane constructed in accordance with the present invention, wherein such membrane is in a generally relaxed configuration.
Figure 9B:
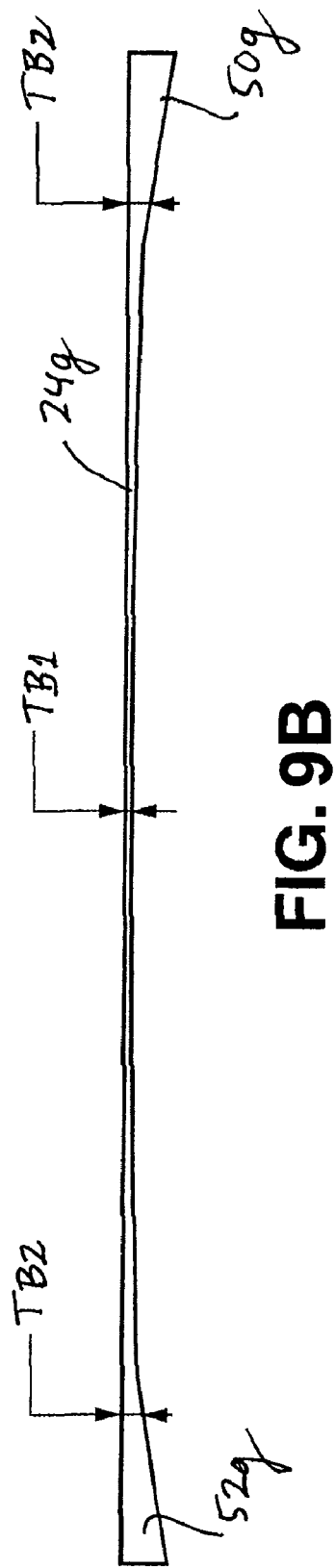
FIG. 9B is a sectional view of the membrane illustrated in FIG. 9A, wherein such membrane is in a stretched, or elongated, configuration.

FIGS. 8, 9A, and 9B show a further alternate embodiment membrane, membrane 24g, having marginal portions 50g, 52g. Portions 50g, 52g do not have flanges 54, 56 as does membrane 24a, discussed above, and could be inserted into pockets, recesses, and/or clips (none shown) in probe P in order to secure membrane 24g to the end of probe P, if desired.

FIG. 9A shows a membrane constructed in accordance with the present invention, such as membrane 24g in a relaxed, unstretched configuration. In this unstretched configuration, the thickness of portion 36g is a first thickness TA1, and or portions 50g, and 52g are of a first thickness TA2. FIG. 9B illustrates the membrane in a stretched configuration, such as would be the case when the membrane is stretched upon application to the end of probe P. Note the reduced thickness of portion 36g at TB1 and at portions 50g and 52g, at TB2. It is to be understood that each of the membranes of the present invention have similar such stretching or elongation characteristics.

Figures 10A, 10B:
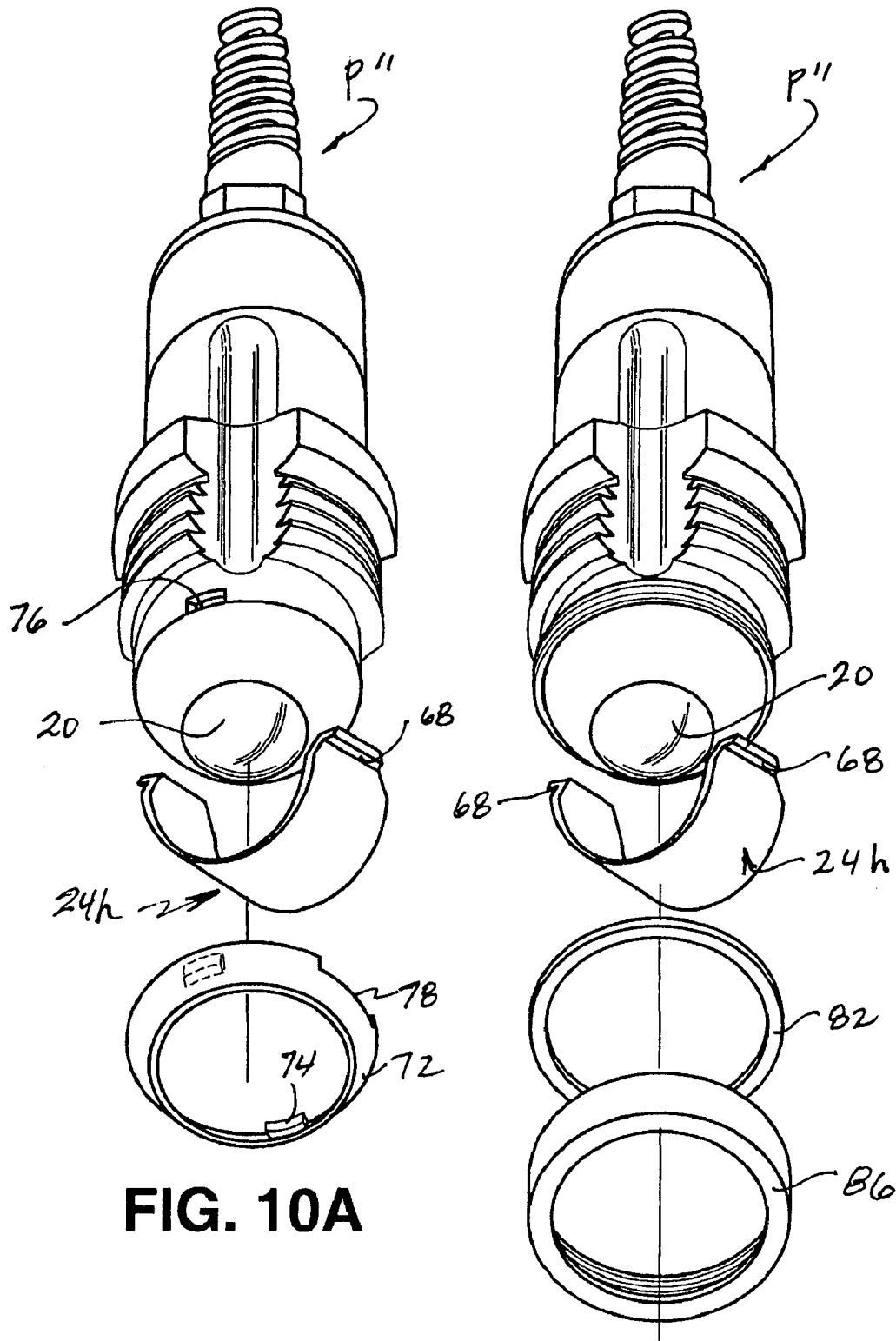
FIG. 10A is an exploded view of a second alternate embodiment probe embodying the oxygen sensing system of the present invention, wherein a ring is provided for securing a seventh alternate embodiment membrane to such probe.
FIG. 10B is an exploded view of a third alternate embodiment probe embodying the oxygen sensing system of the present invention having a threaded ring and a washer for attaching the seventh alternate embodiment to such probe.

FIGS. 10A and 10B illustrate additional alternate embodiments of a membrane, specifically, membrane 24h. Membrane 24h includes outwardly extending ears 68 respectively, which are engaged by a coupler, generally 70, for releasably attaching membrane 24h to the end of alternate embodiment probe P'''. As shown in FIG. 10A, coupler 70 includes a snap ring 72 having resilient prongs 74 which releasably engage with pockets 76 proximate the end of probe P. Snap ring 72 includes recesses 78 for receipt of ears 68 of membrane 24h.

FIG. 10B illustrates coupler 70 as including a threaded arrangement having a washer 82 which bears against ears 68 of membrane 24h upon attachment of membrane 24h to the end of probe P'''. Probe P''', as shown in FIG. 10B includes a threaded portion 84 which threadingly receives a ring 86 having circumferentially extending threads 88. Upon positioning of ring 86, washer 82, and membrane 24h with respect to one another, membrane 24h is attached to the end of probe P''' by threading ring 86 onto threads 88 of probe P''' and tightening ring 86.

Figure 13A:
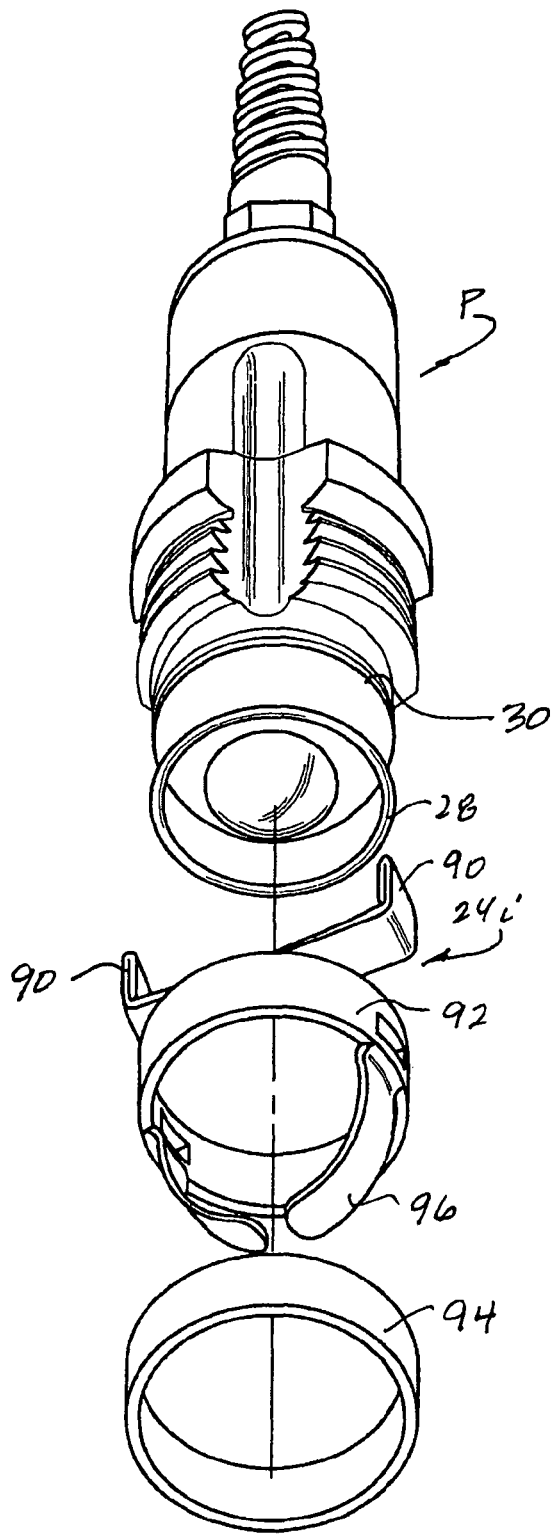
FIG. 13A is an exploded view of a third alternate embodiment probe embodying the oxygen sensing system of the present invention, including a guard member and a ring member for attachment to the probe.
Figure 13B:
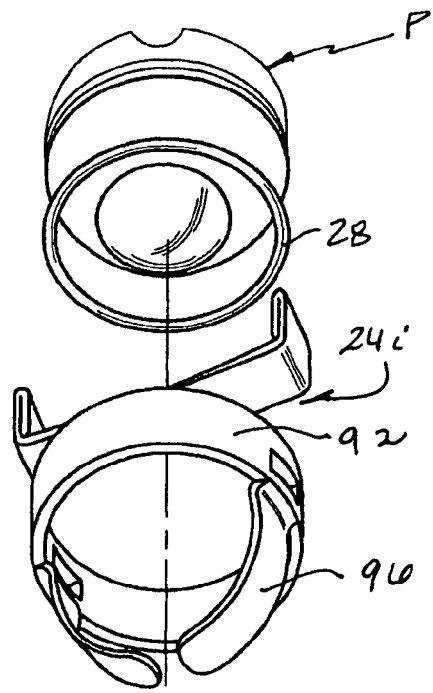
FIG. 13B is an exploded view of a fourth alternate embodiment probe embodying the oxygen sensing system of the present invention, including a guard member and a ring member for attachment to the probe.

FIGS. 13A-13D illustrate additional alternate embodiments of a membrane, specifically, membrane 24i. Membrane 24i includes folded-over end portions 90, which are engaged by a coupling arrangement for releasably attaching membrane 24i to the end of probe P. As shown in FIG. 13A, an O-ring 28 is inserted into groove 30 of probe P, and the end portions 90 are placed against O-ring 28. A resilient ring 92 is placed about membrane 24i and O-ring 28, and an outer slip ring 94 is applied around ring 92, to hold membrane 24i in place on the end of probe P. Ring 92 also includes guard members 96 which extend outwardly over and beyond membrane 24i to both protect membrane 24i from impact and mechanical and/or physical damage, and to also block out, to a certain extent, unwanted ambient light form membrane 24i, while sufficient fluid flow about membrane 24i during use during use. As shown in FIG. 13B, ring 92 can be used without slip ring to hold membrane 24i in place, if desired.

Figure 13C:
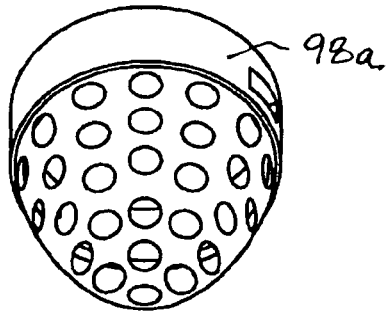
FIG. 13C is a perspective view of a first alternate embodiment guard member.
Figure 13D:
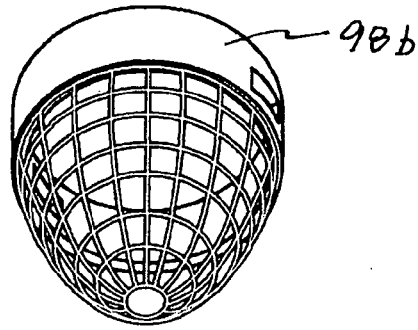
FIG. 13D is a perspective view of a second alternate embodiment guard member.

FIGS. 13C and 13D illustrate additional embodiments for attaching membrane 24i to the end of probe P, wherein, as compared to the embodiment discussed above and shown in FIG. 13A, ring 92 and slip ring 94 are replaced by a guard 98a, as shown in FIG. 13B, and, as shown in FIG. 13D, by guard 98b. Guard 98a is dome-shaped and is perforated and protects membrane 24*i* from impact and mechanical and/or physical damage, and to also block out, to a certain extent, unwanted ambient light from membrane 24*i*, while permitting adequate fluid flow about membrane 24*i* during use. Guard 98*b* operates in similar manner as does guard 98*a*, but guard 98*b* is of a screen and/or mesh construction.

Figure 14:
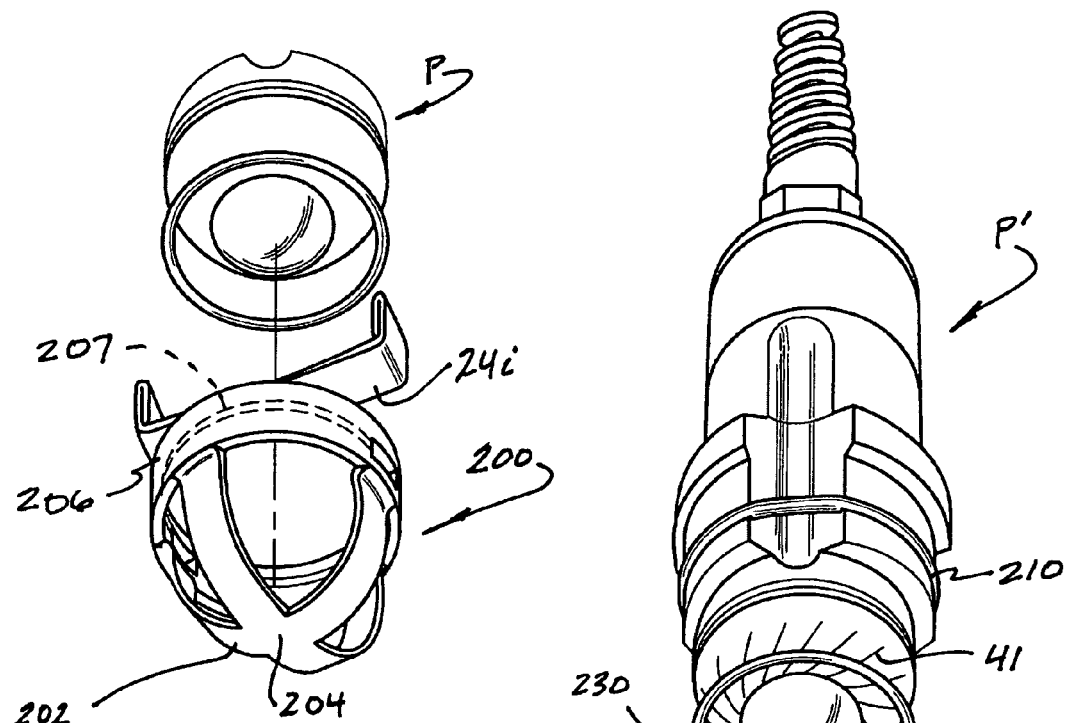
FIG. 14 is exploded view of a fifth alternate embodiment probe embodying the oxygen sensing system of the present invention, including a combination guard member and ring member for attachment to the probe.

FIG. 14 shows another alternate embodiment probe embodying the oxygen sensing system of the present invention, including a combination guard member and ring member, generally 200, for attachment to the end of probe P. Combination member 200 includes a cross-shaped guard 202 which includes a surface 204 which acts to protect a membrane, such as membrane 24*i*, from external light exposure and from potentially damaging contact with an external object or source. Combination member 200 also includes a ring member portion 206, which includes an internal circumferentially extending groove 207 that receives an O-ring 28 on the end of probe P in a snap-fit relationship. This snap-fit retains combination member 200 on the end of probe P during use.

FIG. 15 shows a still further embodiment of the oxygen sensing system of the present invention, having a collar 208 which attaches to the end of probe P' with a snap-fit arrangement. An O-ring 210 is received in a groove of probe P' and is received in an internal circumferentially extending groove 212 of collar 208, instead of in a threaded relationship as is collar 100.

FIG. 15 also shows a guard, generally 220, having a ring member 222 which includes a groove 224 for receiving O-ring 28 on probe P', to allow a snap-fit connection of guard 220 to the end of probe P'. Ring member 222 includes notches 223 which receive the feet 230 of legs 232 of a guard, generally 234. Guard 234 includes a plate 236, to which legs 232 are attached, and serves to protect the membrane 24*j* (which functions as do membranes 24-24*i* discussed herein) from physical damage and from excessive external light. Membrane 24*j* is received in slots in ring member 222 and includes enlarged end portions 240 which retain membrane 24*j* within ring member 222. Although ring member 222 and guard 234 are illustrated as being separate members, in one preferred embodiment, such members are integral with one another.

As best shown in FIGS. 2A and 2B, probe P includes a collar 100 for reducing ambient light exposure onto a membrane constructed in accordance with the present invention, such as, membrane 24*a*, while still allowing adequate flow of fluid around the end of the probe and the membrane for taking accurate readings. In one preferred embodiment, probe P includes elongated channels, generally 102, extending longitudinally about the circumference of probe P and channels 104 extending longitudinally in the interior of collar 100. Channels 102 are adjacent threaded lands 106, and collar 100 is threadingly engaged with threaded lands 106. Channels 102 and 104 allow water to flow to and fro therein as the probe P is oscillated in a fluid source while taking a measurement. Alternately, as noted above, if probe P is static while taking measurements, the fluid is permitted come into contact with the membrane. In one preferred embodiment, collar 100 extends outwardly beyond the extreme end of the sensor.

Collar 100 allows fluid flow to be improved around the membrane, i.e., on both sides of such membrane, thereby potentially improving the measurement technique using probe P, and also simultaneously diminishes undesirable ambient light exposure to the sensor. In an alternate embodiment, collar 100 could be provided, if desired, with a flexible membrane or adjustable aperture (not shown) at the open end of collar 100 in order to further reduce ambient light exposure to the membrane.

Figure 11:
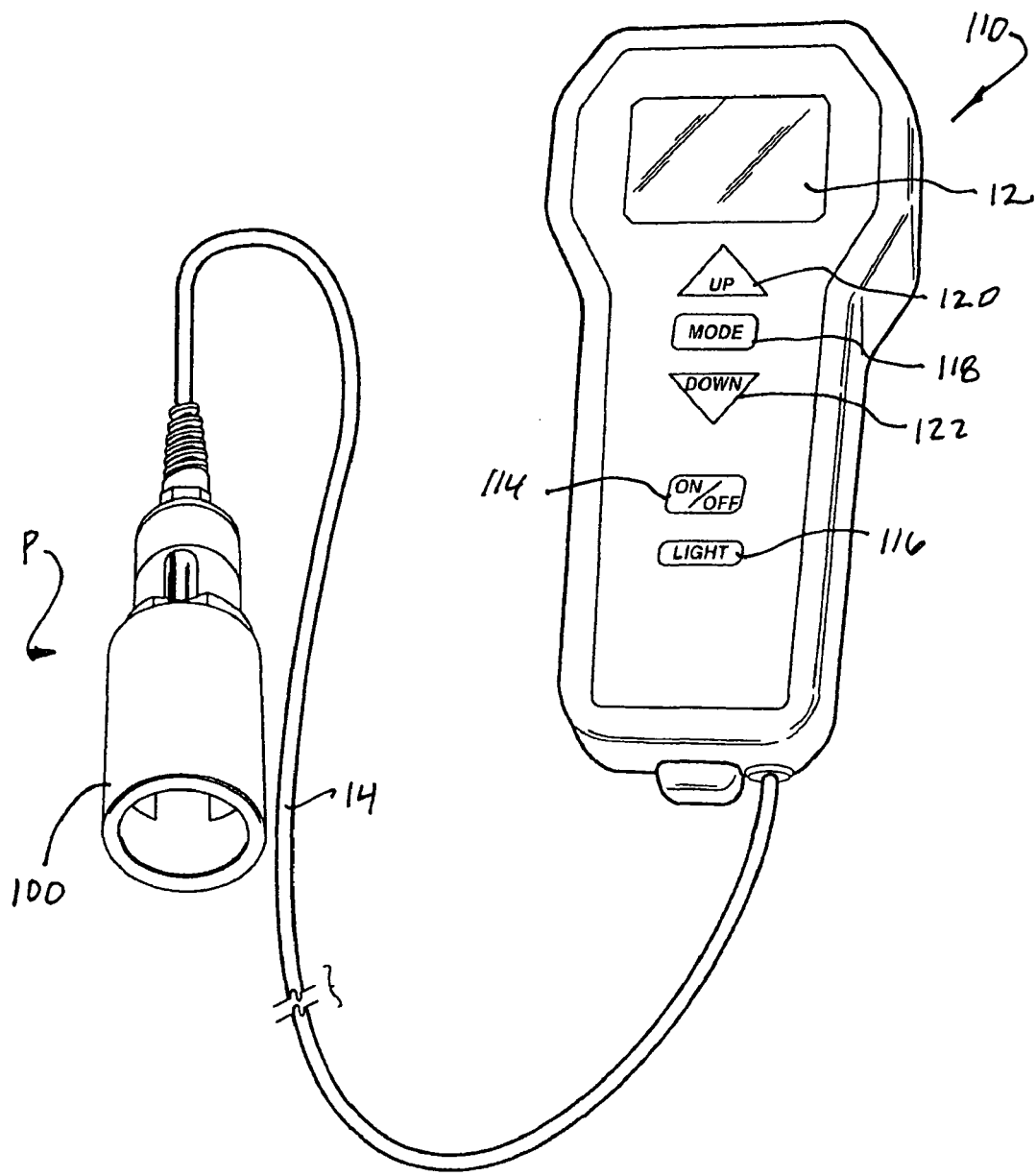
FIG. 11 is a perspective view of a hand-held probe constructed in accordance with the present invention.
Figure 12:
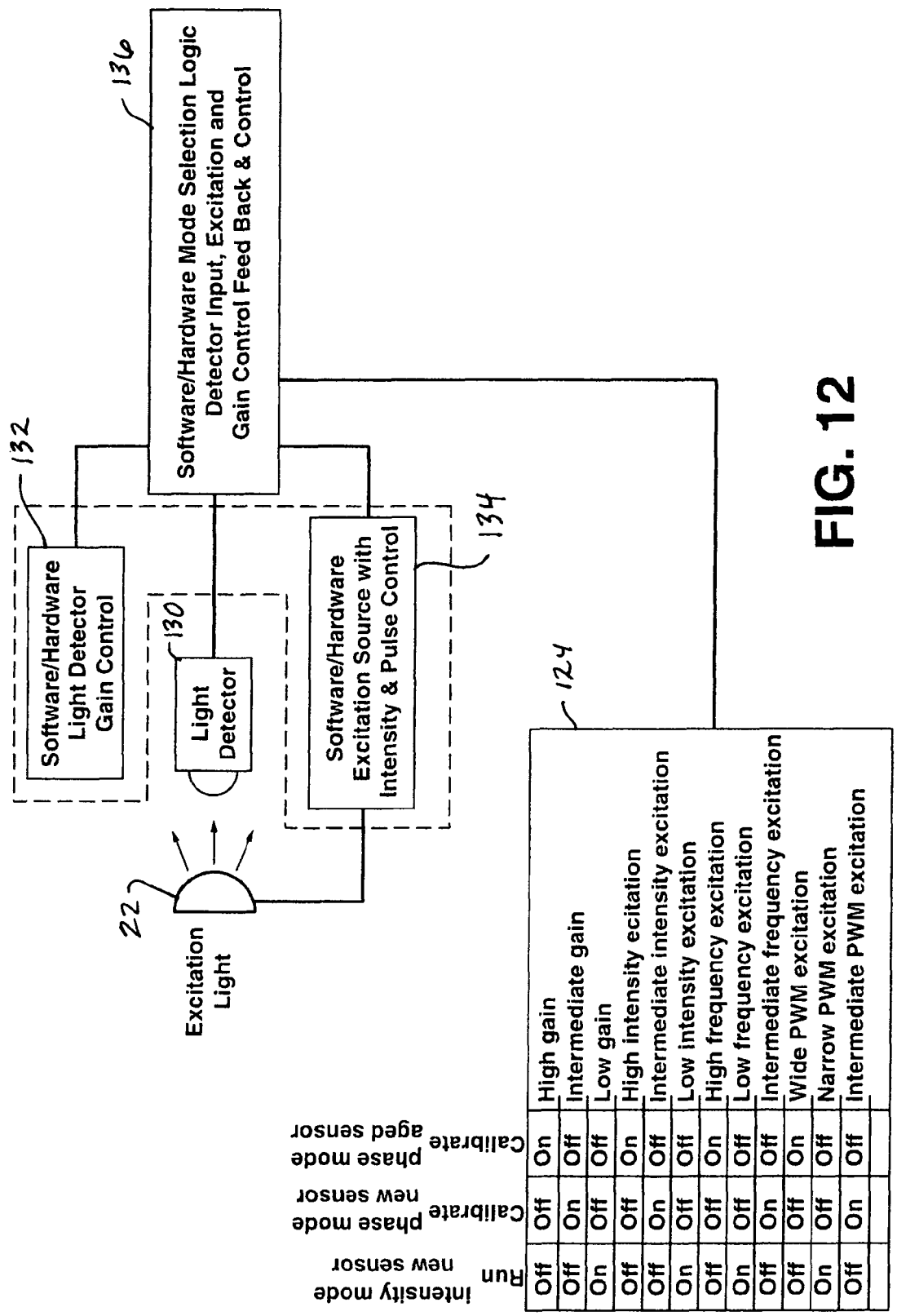
FIG. 12 is a schematic representation of an oxygen sensing system constructed in accordance with the present invention.

Turning to FIGS. 11 and 12, sensing system 10 is illustrated in a portable, hand-held configuration. Probe P, having a collar 100 attached thereto, is connected to a hand-held controller 110 via cable 14. Hand-held controller 110 includes a display window which could be of a light emitting diode (LED) construction, liquid crystal display (LCD) construction, plasma screen, cathode ray tube (CRT), analog display (such as a moving pointer, needle, etc.) or of some other construction. Display 112 could output readings such as the temperature of the fluid being sensed by probe P, the oxygen content, or other constituent content of the fluid being measured, elevation, ambient temperature, time, geographic coordinates (such as through use of a global positioning satellite (GPS) capability), a timer, etc. Controls for controller 110 could include a power switch 114, a light switch 116, a menu or mode switch 118, and up and down switches 120, 122 respectively, for making selections within multiple modes and/or menu items. Sensing system 10 can be used, in one particular application, for sensing the oxygen content in sewage being treated, as illustrated in FIG. 1.

FIG. 12 illustrates schematically the potential configurations of controller 110 and probe P. Table 124 illustrates operation of probe P in an intensity mode, with a new sensor, or membrane, a calibrate mode in a lifetime/phase shift, or "phase" mode using a new membrane, and a calibration mode, again in the phase mode, using an aged membrane. Depending on such selected operational parameter, the electronics of controller 110 and the electronics supporting of probe P are manipulated based on varying gains, such as high gain, intermediate gain, or low gain; intensity, such as high intensity excitation in the respective control of light detector 130 based on high intensity excitation, intermediate intensity excitation, low intensity excitation, high frequency excitation, low frequency excitation, intermediate frequency excitation, wide pulse wave modulation (PWM) excitation, narrow PWM excitation, and/or intermediate PWM excitation. Table 124 also illustrates the respective toggling on or off of such gain and excitation parameters depending on whether system 10 is finning in intensity mode with a new sensor, or calibrating in a phase mode with a new or aged sensor membrane.

System 10 includes software and hardware, generally 132, programmed for controlling the gain of light detector 30, and also includes software and hardware, generally 134, for controlling the excitation source of excitation light with intensity and/or pulse control. Additionally, system 10 includes software and hardware, generally 136, programmed for allowing controller 110 to provide modes and logic for selection of light detector 130 input, excitation levels, gain control feedback, and overall control.

As noted above, a disadvantage of intensity-based systems is that due to the photo bleaching aspect of the material, calibration is generally required more frequently than would be the case with lifetime/phase-shift-based sensors operating in the same environment. Ideally, for an intensity based system, the sensor material would be pretreated by pre-photo bleaching, since, in such intensity based system, it would be desired that the sensor material already be photo bleached to the fullest extent prior to being put into use. Since the sensor material may be relatively unstable, the sensor is prone to variation over the life of the sensor. Application of the Stern-Volmer equation (discussed in the Bacon et al. patent), which essentially holds that the intensity of fluorescent of the sensor is inversely proportional to the oxygen concentration, allows the oxygen content to be measured and derived based on the detected intensity of the sensor.

The method of the present invention preferably uses the intensity based measuring system as its prime measurement means, but it uses on an intermittent basis a lifetime/phase-shift-type sensor in order to calibrate the intensity based system. It is anticipated that upon installation of such a system, the lifetime based sensor would eliminate the need to pre-photo bleach the intensity based sensor, and doing it in situ, thereby potentially eliminating a pre-photo bleaching manufacturing process.

With regards to the method for auto-calibration in situ, only one membrane constructed in accordance with the present invention is required. A combination of hardware and software would allow such membrane to be used in both modes, both the lifetime/phase-shift mode and the intensity mode.

It is further anticipated that upon initial installation of the intensity based sensor, the calibration by the lifetime-type membrane will be more frequent until it is determined that the necessary calibration adjustment of the intensity of the probe P becomes negligible, i.e., becomes stabilized. Once it is determined that the membrane probe P has become "photo bleached" in situ, and thus stabilized, then the frequency of the calibration by the lifetime/phase-shift aspect of probe P would likely decrease to long-term, predetermined specified intervals.

Another advantage of in situ calibration is that, presently, conventional sensors must be oftentimes removed from their environment, such as in a sewage treatment tank, and air calibrated, which involves the measurement of ambient temperature, entering the known elevation, and then using standardized tables to determine the ambient oxygen content.

Ideally, the calibration by the lifetime/phase-shift aspect of the probe would occur when the oxygen levels sensed by the intensity based aspect of the probe are less than the point where the signal-to-noise ratio is at an advantageous level for lifetime measurements, which, in the case of oxygen, could typically be between ambient and zero percent concentration.

Another advantage of the present invention is that because the lifetime/phase-shift portion of this membrane is used only infrequently, it is less prone to photo-bleaching over time, and, accordingly, should have a life that approximates the life of the intensity-based membrane.

Fluorescent measurement techniques can also be used in detecting pH, carbon monoxide, levels of various gases, different aqueous components, elemental components, and macromolecular components, especially in genetics and the biotech industries.

While preferred embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the present disclosure.

What is claimed is:

1. A sensor for reflecting excitation light from a light source used in an oxygen sensing system, the sensor comprising:
   a silicon-based, elastic body portion having a central portion and peripheral portions positioned on either side of said central portion;
   said central portion being configured for reflecting the excitation light from said light source used in said oxygen sensing system and being of a first thickness;
   said peripheral portions being of a second thickness; and
   said second thickness being of substantially greater thickness than said first thickness.

2. The sensor as defined in claim 1, further comprising:
   an O-ring that attaches said body portion to the oxygen sensing system.

3. The sensor as defined in claim 1, further comprising:
   said silicon-based, elastic body portion including ruthenium.

4. The sensor as defined in claim 1, wherein said peripheral portions are configured to take up and absorb thermal growth of said central portion.

5. The sensor as defined in claim 1, wherein said first thickness is between approximately 0.001 and 0.005 inches.

* * * * *

UNITED STATES PATENT AND TRADEMARK OFFICE
CERTIFICATE OF CORRECTION

PATENT NO. : 7,926,322 B1  Page 1 of 1
APPLICATION NO. : 11/983598
DATED : April 19, 2011
INVENTOR(S) : James C. Queen It is certified that error appears in the above-identified patent and that said Letters Patent is hereby corrected as shown below:

Column 10, line 40: the word "finning" should be changed to "running"

Signed and Sealed this
Fifth Day of July, 2011

David J. Kappos
*Director of the United States Patent and Trademark Office*